(12) United States Patent
Lahlouh et al.

(10) Patent No.: US 9,276,261 B2
(45) Date of Patent: Mar. 1, 2016

(54) SURFACE TREATED SILICON CONTAINING ACTIVE MATERIALS FOR ELECTROCHEMICAL CELLS

(71) Applicant: Nexeon Limited, Abingdon (GB)

(72) Inventors: John Lahlouh, San Jose, CA (US); Klaus Joachim Dahl, Atherton, CA (US); Sarah Lynn Goertzen, Sunnyvale, CA (US); Marie Kerlau, Sunnyvale, CA (US)

(73) Assignee: Nexeon Limited (GB)

( * ) Notice: Subject to any disclaimer, the term of this patent is extended or adjusted under 35 U.S.C. 154(b) by 0 days.

(21) Appl. No.: 14/597,554

(22) Filed: Jan. 15, 2015

(65) Prior Publication Data

US 2015/0125595 A1 May 7, 2015

Related U.S. Application Data

(63) Continuation of application No. 14/093,666, filed on Dec. 2, 2013, now abandoned.

(60) Provisional application No. 61/826,597, filed on May 23, 2013.

(51) Int. Cl.
*H01M 4/13* (2010.01)
*H01M 4/36* (2006.01)
(Continued)

(52) U.S. Cl.
CPC ............ *H01M 4/366* (2013.01); *G01N 27/403* (2013.01); *H01M 4/0402* (2013.01); *H01M 4/0404* (2013.01); *H01M 4/0471* (2013.01); *H01M 4/139* (2013.01); *H01M 4/1395* (2013.01);
(Continued)

(58) Field of Classification Search
None
See application file for complete search history.

(56) References Cited

U.S. PATENT DOCUMENTS 7,402,829 B2 7/2008 Green
7,846,583 B2 12/2010 Oh et al.
(Continued)

FOREIGN PATENT DOCUMENTS

CN 102299306 A 12/2011
JP 2004281317 A 10/2004
WO 2014189923 A1 11/2014

OTHER PUBLICATIONS

Magasinski et al., Toward efficient binders for Li-Ion battery Si-based anodes: polyacrylic acid, ACS Appl. Mater. Interfaces, 2(11), 2010, pp. 3004-3010.*

(Continued)

*Primary Examiner* — Patrick Ryan
*Assistant Examiner* — Jose Colucci Rios
(74) *Attorney, Agent, or Firm* — Kwan & Olynick LLP

(57) ABSTRACT

Provided are active materials for electrochemical cells. The active materials include silicon containing structures and treatment layers covering at least some surface of these structures. The treatment layers may include aminosilane, a poly (amine), and a poly(imine). These layers are used to increase adhesion of the structures to polymer binders within active material layers of the electrode. As such, when the silicon containing structures change their size during cycling, the bonds between the binder and the silicon containing structure structures or, more specifically, the bonds between the binder and the treatment layer are retained and cycling characteristics of the electrochemical cells are preserved. Also provided are electrochemical cells fabricated with such active materials and methods of fabricating these active materials and electrochemical cells.

19 Claims, 6 Drawing Sheets

(51) Int. Cl.
*G01N 27/403* (2006.01)
*H01M 4/04* (2006.01)
*H01M 4/139* (2010.01)
*H01M 4/38* (2006.01)
*H01M 4/62* (2006.01)
*H01M 10/0525* (2010.01)
*H01M 4/1395* (2010.01)

(52) U.S. Cl.
CPC ............. *H01M 4/386* (2013.01); *H01M 4/621* (2013.01); *H01M 4/622* (2013.01); *H01M 4/625* (2013.01); *H01M 10/0525* (2013.01); *Y02E 60/122* (2013.01)

(56) References Cited

U.S. PATENT DOCUMENTS

| | | | |
|---|---|---|---|
| 2008/0261112 A1 | 10/2008 | Nagata et al. | |
| 2008/0311464 A1* | 12/2008 | Krause et al. | 429/50 |
| 2009/0053606 A1 | 2/2009 | Kim et al. | |
| 2009/0286157 A1* | 11/2009 | Chen et al. | 429/209 |
| 2009/0305139 A1* | 12/2009 | Oh et al. | 429/231.8 |
| 2010/0190061 A1 | 7/2010 | Green | |
| 2010/0285358 A1 | 11/2010 | Cui et al. | |
| 2010/0297502 A1 | 11/2010 | Zhu et al. | |
| 2011/0067228 A1 | 3/2011 | Green | |
| 2011/0117431 A1 | 5/2011 | Fukui et al. | |
| 2011/0136008 A1 | 6/2011 | Hirose et al. | |
| 2011/0250498 A1 | 10/2011 | Green et al. | |
| 2011/0269019 A1 | 11/2011 | Green et al. | |
| 2012/0028117 A1* | 2/2012 | Plee et al. | 429/211 |
| 2012/0094178 A1 | 4/2012 | Loveridge et al. | 429/217 |
| 2012/0121981 A1* | 5/2012 | Harimoto et al. | 429/213 |
| 2014/0346618 A1 | 11/2014 | Lahlouh et al. | |

OTHER PUBLICATIONS

"U.S. Appl. No. 14/093,666, Examiner Interview Summary mailed Aug. 27, 2014", 3 pgs.

"U.S. Appl. No. 14/093,666, Final Office Action mailed Oct. 16, 2014", 27 pgs.

"U.S. Appl. No. 14/093,666, Non Final Office Action mailed Mar. 6, 2014", 17 pgs.

"Int'l Application Serial No. PCT/US2014/038780, Search Report and Written Opinion mailed Oct. 30, 2014", 6 pgs.

Lahlouh, John et al., "Surface Treated Silicon Containing Active Materials for Electrochemical Cells", U.S. Appl. No. 14/093,666, filed Dec. 2, 2013, 37 pgs.

Magasinski, et al., "Toward Efficient Binders for Li-Ion Battery Si-Based Anodes: Polyacrylic Acid", ACS Appl. Mater. Interfaces, 2(11), 2010, pp. 3004-3010.

* cited by examiner

SURFACE TREATED SILICON CONTAINING ACTIVE MATERIALS FOR ELECTROCHEMICAL CELLS

CROSS-REFERENCE TO RELATED APPLICATIONS

This application is a continuation application of U.S. Ser. No. 14/093,666, entitled: "SURFACE TREATED SILICON CONTAINING ACTIVE MATERIALS FOR ELECTROCHEMICAL CELLS" filed on 2 Dec. 2013, which claims the benefit under 35 U.S.C. §119(e) of U.S. Provisional Patent Application 61/826,597, entitled: "SURFACE TREATED SILICON CONTAINING ACTIVE MATERIALS FOR ELECTROCHEMICAL CELLS" filed on 23 May 2013, both of which are incorporated herein by reference in their entirety.

BACKGROUND

Rapid development of mobile electronics, electrical vehicles, medical devices, and other like application demands high capacity rechargeable batteries that are light and small yet provide high storage capacity and electrical currents. Lithium ion technology presented some advancement in this area in comparison, for example, to lead-acid and nickel metal hydride batteries. However, to date, lithium ion cells are mainly built with graphite as a negative active material. Graphite's theoretical capacity is 372 mAh/g, and this fact inherently limits further improvement.

Silicon, germanium, tin, and many other materials are potential candidates for replacement of graphite because of their high lithiation capacities. For example, silicon has a theoretical capacity of about 4200 mAh/g, which corresponds to the $Li_{4.4}Si$ phase. Yet, adoption of these materials is limited in part by substantial changes in volume during cycling. For example, silicon expands by as much as 400% when charged to its theoretical capacity. Volume changes of this magnitude can cause stresses in the electrode, resulting in fractures and pulverization of active materials, losses of electrical and mechanical connections within the electrode, and capacity fading.

SUMMARY

Provided are active materials for electrochemical cells. The active materials include silicon containing structures and treatment layers covering at least some surface of these structures. The treatment layers may include aminosilane, a poly(amine), and a poly(imine). These layers are used to increase adhesion of the structures to polymer binders within active material layers of the electrode. As such, when the silicon containing structures change their size during cycling, the bonds between the binder and the silicon containing structure structures or, more specifically, the bonds between the binder and the treatment layer are retained and cycling characteristics of the electrochemical cells are preserved. Also provided are electrochemical cells fabricated with such active materials and methods of fabricating these active materials and electrochemical cells.

In some embodiments, an active material for use in electrochemical cells includes a silicon containing structure and a treatment layer. The silicon containing structure includes an external surface. The treatment layer covers at least a portion of the external surface of the silicon containing structure. The treatment layer includes one or more of the following treatment materials: an aminosilane, a poly(amine), and a poly(imine). More specific examples of the treatment materials include aminopropyltriethoxysilane, aminopropylmethoxysilane, bis-gamma-trimethoxysilypropyl amine, aminoneohexyltrimethoxysilane, and aminoneohexylmethyldimethoxysilane. In some embodiments, a treatment material is one of poly(ethyleneimine), poly(allylamine), or poly(vinylamine). The silicon containing structure may have one of the following shapes: particles, flakes, and rods.

In some embodiments, the volume ratio of the treatment layer to the silicon containing structure is between about 0.001% and 10%. More specifically, the volume ratio of the treatment layer to the silicon containing structure is less than about 0.1%. In some embodiments, the treatment layer is formed by molecules of the one or more treatment materials adsorbed on the external surface of the silicon containing structure. The treatment layer may be also formed by molecules of the one or more treatment materials covalently bound to the external surface of the silicon containing structure. In some embodiments, the treatment material includes aminosilane. The one or more treatment materials may form oligomeric brushes extending away from the external surface of the silicon containing structure.

In some embodiments, the silicon containing structure includes a silicon alloy. The active material may also include a carbon containing layer covering at least a portion of the treatment layer. The carbon containing layer may include multiple carbon particles adsorbed or covalently bound to the treatment layer. In some embodiments, the external surface of the silicon containing structure includes silicon dioxide.

Provided also is a method of fabricating an active material for use in electrochemical cells. The method may involve preparing a solution that includes a carrier solvent and one or more of the following treatment materials: an aminosilane coupling agent, a poly(amine), and a poly(imine). The method may proceed with combining the solution with silicon containing structures. The acidity of the solution is maintained at between about 4.0 pH and 6.0 pH for the aminosilanization. The method may proceed with removing the carrier solvent while retaining the one or more treatment materials on external surfaces of the silicon containing structures. Removing of the carrier solvent may be performed at a temperature of between about 40° C. and 80° C. In some embodiments, the method also involves performing a heat treatment on the silicon containing structures and the one or more treatment materials. The heat treatment adoptively or covalently anchors the one or more treatment materials to the external surfaces of the silicon containing structures. The heat treatment may be performed at a temperature of between about 80° C. and 130° C. In some embodiments, the method may also involve combining the solution with carbon containing structures such that the carbon containing structures form a layer over the silicon containing structures.

Also provided is a method of fabricating an electrode for use in electrochemical cells. The method involves forming a slurry including an active material and a binder. The active material includes silicon containing structure individually covered with a layer of one or more of the following materials: an aminosilane, a poly(amine), and a poly(imine). The binder may include poly acrylic acid (PAA). The method may proceed with coating the slurry onto a substrate and drying the slurry.

These and other embodiments are described further below with reference to the figures.

DETAILED DESCRIPTION

Figure 1:
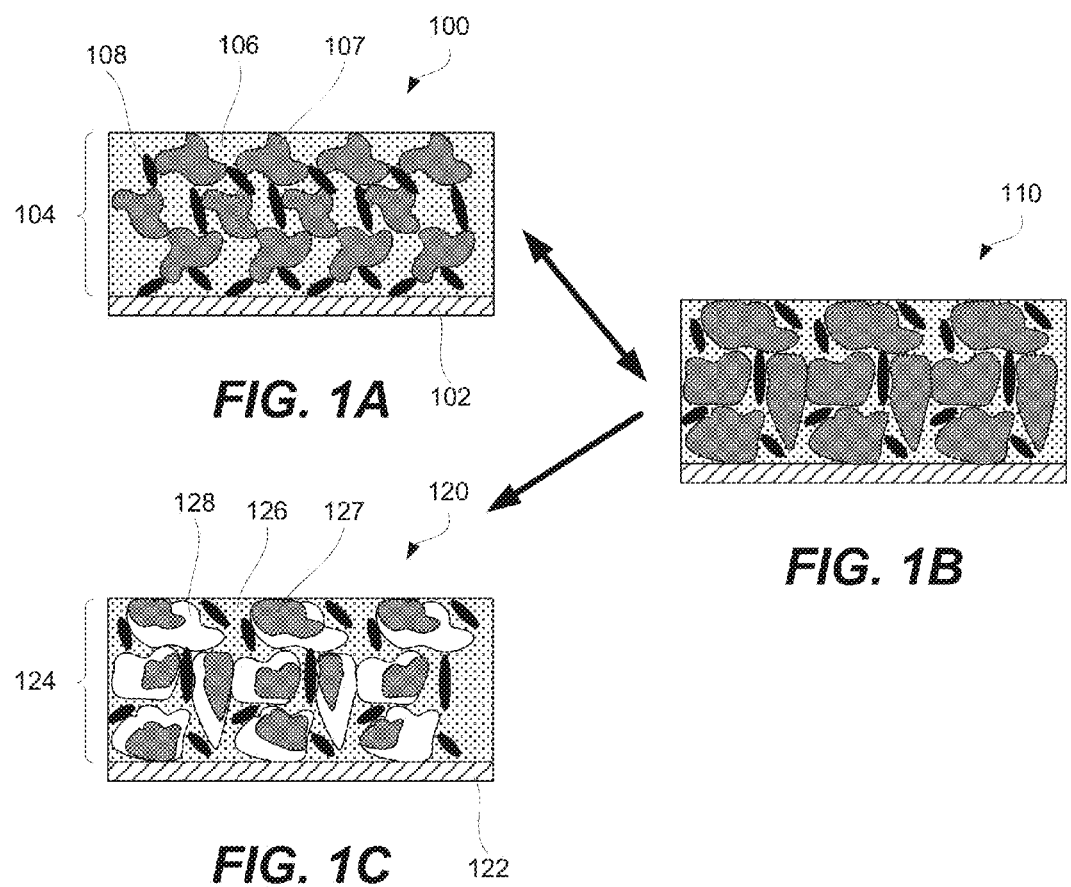
FIG. 1A is a schematic illustration of an electrode prior to first charging, in accordance with some embodiments.
FIG. 1B is a schematic illustration of the electrode in FIG. 1A after the initial charging, in accordance with some embodiments.
FIG. 1C is a schematic illustration of the electrode in FIGS. 1A and 1B after discharging showing voids within an active material layer caused by contracting of the active material particles, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

The capacity of a lithium ion battery can be substantially increased by partial or complete replacement of carbon-based active materials with silicon based materials and/or other similar high capacity materials, such as tin and germanium. However, integration of these high capacity materials into battery electrode has proved to be challenging because of volume changes that these materials experience during lithiation. Previous integration approaches focused on reducing the size of silicon containing structures and combining these structures with other materials to reduce volume change effects. However, these approaches led to low capacity designs and inefficient use of silicon. Similar approaches haven been tried with other high capacity material.

This volume change during lithiation also causes significant challenges in selecting a binder, which can be effectively used with such dynamic active materials. A binder is used to hold active material structures together in an electrode layer and attached to a substrate. Poly-vinylidene fluoride (PVDF) is the most common binder for lithium ion cells. When combined with silicon structures, PVDF molecules and the silicon structures are bound by weak van der Waals forces and fail to accommodate large volume changes of the structures. As such, PVDF shows poor performance in holding the silicon structures together and maintaining mechanical and electrical connections between the structures, which results in capacity fading. Likewise, binders that have only hydroxyl functional groups or carbonyl functional groups, such as polyvinyl alcohol (PVA) and polyacrylamide (PAM), do not exhibit enough binding strength to silicon particles when the silicon particles expand and contract during cycling.

It has been found that certain surface treatments of silicon containing structures can significantly improve performance of lithium ion cells when used with certain binders. Specifically, silicon containing structures can be treated with various aminosilanes, poly(amines), and/or poly(imines) to modify the surface of the structures and to improve adhesion of these structures to the specific binders. Specific examples of suitable treating agents include, but not limited to, aminopropyltriethoxysilane, aminopropyltrimethoxysilane, bis-gamma-trimethoxysilypropyl amine, aminoneohexyltrimethoxysilane, aminoneohexylmethyldimethoxysilane, poly(ethyleneimine), poly(allylamine), and poly(vinylamine). For example, SILQUEST® Y-15744, which is an amino-functional organoalkoxysiloxane (available from Momentive Performance Materials Inc. in Columbus, Ohio), may be used for this purpose.

Without being restricted to any particular theory, it is believed that when silicon structures are exposed to air, the structures form a surface layer of silicon dioxide. Similar surface oxidation is experienced by other high capacity active materials, such as germanium and tin. The surface oxidation may occur during handling and processing of these structures, for example, while fabricating electrode for lithium ion batteries. From the conventional standpoint, the surface oxidation may be undesirable because silicon dioxide has a much higher resistivity ($10^{16}$ Ω*m) than silicon ($10^3$ Ω*m).

When the silicon dioxide surface is exposed to water (e.g., in a water based solution of a binder), the surface ionizes and assumes a negative zeta potential, which may be up to −70 mV in some embodiments. A similar phenomenon has been observed with germanium particles and tin. Furthermore, silicon, tin, and/or germanium may be a part of an alloy that includes other components and undergo the same oxidation and surface ionization process as described above. For example, silicon may be alloyed with tin. In general, if oxides of alloying elements are amphoteric, the zeta potential at pH >6 is negative.

Many polymer binders used to support active materials on the substrate, such as polyvinylidene difluoride (PVDF), carboxymethyl cellulose (CMC), styrene butadiene (SBR), alginates, and poly acrylic acid (PAA), may produce negatively charged groups when exposed to solvents. For examples, when PAA dissociates in water at pH >4, it produces negatively charged carboxylate groups along the polymer chains. At lower pH levels, much of the PAA chains are protonated. While these negative charged groups may be used to increase hydrogen in some embodiments, the acidic PAA chains are coiled resulting in a high viscosity of the mixture, often too excessive for adequate processing. At pH level greater than about 9, the PAA chains are elongated to the point where the mixture has too high of a viscosity to permit coating. A solution having a pH of between about 3 and 7 or, more specifically, of between about 4 and 6, such as about 6 may yield an appropriate viscosity for coating. Without being restricted to any particular theory it is believed that adjusting the pH of the PAA binder solution from the levels listed above, e.g., by adding NaOH, increases the viscosity and thereby optimizes the rheology of the casting formulation to permit facile processing Overall, the binder resin may serve several functions. The binder may have high fracture resistance strength and form strong interfacial bonds to the particles of the electrode layer, such as active material particles and/or conductive additive particles. The binder may prevent fracturing within the electrode layer and overcome stresses developed within the layer during charging and discharging. This fracture prevention helps to maintain electronic conduction throughout the layer and between the layer and the current collector. The fracture resistance strength may be enhanced by treating the active material particles. Furthermore, a binder should also allow lithium ion transport through an electrode layer. This ion transport is sometimes referred to as shuttling and occurs between the electrolyte solution and the active material particles of the electrode layer. The ion transport may be facilitated by binders that have carboxylic acid groups. Further, binders capable of dissolving in water, i.e., water-soluble binders are generally preferable because of their lesser environmental impact, simpler processing, and lower cost.

In a typical mixture used to form an electrode layer, negatively charged structures and negatively charged binder molecules repel each other (while in the solution and then in the electrode) resulting in weak interfacial bond strength and fracturing. Specifically, weak bonds between the active material structures and binder molecules result in the active material structures dis-bonding from the binder molecules and losing electrical connections within the electrode and capacity fading. The loss of electrical connections and capacity fading is particularly prominent in electrochemical cells fabricated with high capacity active materials that are susceptible to large volume changes, such as silicon. Furthermore, it should be noted that most carbon-based active materials (or conductive additives) also have a negative zeta potential when dispersed in water.

Surface modification of the active material structures with moieties containing amino groups is believed to impart a positive zeta potential to the structures. In general, various materials, such as aminosilanes or other organic molecules containing primary amines ($NH_2$) and/or secondary amines (NH) or imines can be used. These materials are found to be effective surface modifiers as long as the surface modifying moieties can either be anchored to or adsorbed on the surface of the particle being modified. In some embodiments, anchoring may be achieved by forming chemical bonds. For example, aminosilanes form amide bonds to active material particles, while polyamine adsorb on the surface of the particles. Tertiary amines, such as poly(diallyldimethylammonium chloride), do not form amide bonds but can provide stabilization of particle dispersions. In some embodiments, the modified structures include the amino groups and exhibit the positive zeta potential unlike unmodified structures that may exhibit the negative zeta potential. As such, the modified structures would more readily associate with the negatively charged binder molecules and may even form amide bond between active particles and binder molecules.

Without being restricted to any particular theory, it is believed that moieties with amino groups can be attached to silicon dioxides and other types of surfaces in a number of ways. One attachment type is adsorption of cationic poly (electrolytes), such as poly(ethyleneimine) or poly(allylamine). The poly(electrolyte) may form mono molecular layers on the surfaces of the active material particles. The poly(electrolytes) may be used to treat silicon containing structures and carbon containing structures. Adsorption may be caused by van der Waals (dispersion) forces, hydrogen bonding, and ionic (electrostatic) bonding.

Another attachment type is covalent bonding. For example, aminosilanes are believed to form covalent bonds with the silicon dioxide shell of silicon particles. One molecule of aminosilane can covalently bond to 1 or 2 SiOH groups of that shell. Under certain reaction conditions, the aminosilane forms oligomeric brushes extending away from the silicon dioxide shell. These brushes contain several amino groups.

When large molecules, such as polymers, are used for treatment, the same molecule may form multiple bonding sites on the surface of an active material particle. The bonding sites may extend along the polymer chain and, in some embodiments, provide a mono-molecular layer. The number of bonding sites and the strength of attachment may increase with the molecular weight of a polymer.

Furthermore, sequential layer-by-layer deposition of poly (cations) and poly(anions) may be used to form a multilayered poly(electrolyte salt) structure on the surface of the active material particles. The outermost layer of this multilayered structure may be dominated by the functional groups of the last poly(electrolyte) adsorbed. Without being restricted to any particular theory, it is believed that multilayers provide a more robust surface modification of the active material particles.

Furthermore, it has been found that silicon structures with modified surfaces tend to attract carbon structures, for example, when both types of structures are dissolved in water. As noted above, the modified silicon structure has a positive zeta potential while carbon may have a negative zeta potential. By controlling the size of silicon structures and carbon structures, composite structures with silicon cores and carbon shells may be formed. For example, silicon particles may be between about 1 and 50 microns in size or, more specifically, between about 2 and 10 micrometers in size, while carbon particles can be less than about 1 micrometer in size or, more specifically, less than about 0.2 micrometers in size. These core-shell structures may be formed before mixing slurry for coating an electrode, for example, during a treatment process. Alternatively, the core-shell structures are formed while mixing the slurry, such as during electrode fabrication operations. The silicon core—carbon shell structure may include silicon-containing core, silicon dioxide layer around its core, treatment layer containing amine, imine, or other groups, and then an outer carbon layer. It should be noted that these layers do not have to be continuous and form a complete shell.

Composite structures including silicon cores and conductive carbon shells have shown improved performance relative to uncoated silicon particles in terms of capacity and stability of lithium ion cells. However, previously proposed processes by which these composite structures are made are expensive and hard to control. For example, one previous proposal involves dispersing silicon particles in a resorcinol/formaldehyde mixture and then polymerizing the phenolic resin with embedded silicon particles. The polymers is then pyrolyzed in nitrogen (or argon) to form carbon coating on the silicon particles and the pyrolysis products are ground to form fine particles for use in electrode fabrication operations.

Bonding between the active materials particles and the binder in an electrode and its effect on the cycle life will now be described with reference to FIGS. 1A-1C. Specifically, FIG. 1A is a schematic illustration of an electrode 100 in its discharge state, in accordance with some embodiments. Electrode 100 includes a current collector substrate 102 and an active material layer 104 disposed over and adhered to current collector substrate 102. Active material layer 104 also includes binder 106 and active material structures 107. In some embodiments, active material layer 104 may also include conductive additive 108, such as conductive carbon additive. When lithium is added to active material structures 107, these structures 107 may increase in size as shown by a transition from FIG. 1A to FIG. 1B. Electrode 100 shown in FIG. 1A may be referred to as a discharged electrode, while electrode 110 shown in FIG. 1B may be referred to as a charged electrode. The terms "charged" and "discharged" are relative and correspond to relative amounts of lithium in the electrodes or, more specifically, in active material structures. Addition of lithium into the active material structures may cause swelling of these structures. For example, silicon structures swell by as much as 400% when charged to silicon's theoretical capacity. As the active materials particles swell, they push on other components of the active material layer and rearrange these other components in the layer. Examples of these other components include binder and conductive additive particles, when these particles are used. In some embodiments, the thickness of the active material layer may also change.

When lithium is removed during discharge, the active material particles shrink and pull away from other components of the active material layer. If the bonding between the active material particles and the binder is sufficiently strong, these shrinking active material particles will pull these other components and may retain mechanical and, as a result, electrical connections with these other components. Even though some changes may occur within the active material layer during each charge-discharge cycle, as long as these changes do not electrically disconnect a significant portion the active material particles from the current collector substrate, the capacity of the electrode will remain substantially the same. As such, the bonding strength between the active material particles and binder molecules is believed to play an important role in capacity retention, particularly when high capacity active materials are used.

However, if the bonding strength between the active material structures and the binder is weak, the discharge process may cause some active materials structures or clusters of the active material structures to become electrically disconnected from the current collector substrate. As a result, these structure and/or clusters are not exposed to an operating potential of the negative electrode and do not contribute to the capacity during subsequent cycling. This phenomenon is schematically presented in FIG. 1C. Specifically, FIG. 1C illustrates an electrode in which voids 128 exists within active material layer 124. The voids may be between binder 126 and active material structures 127, between adjacent active material structures 127. Voids 128 may be created when active material structures 127 first swell during charge and push away other components and then shrink during discharge without being able to pull other components and fill the entire volume previously occupied by the swollen active material particles. Voids 128 may cause active material structures 127 become disconnected from current collector substrate 122 and not contribute to cycling capacity.

Without being restricted to any particular theory, it is believed that a combination of strong adhesion between active material particles and binder as well as a high tensile strength of the binder helps to maintain electrical connections within an active material layers needed for long cycle life. While elastic binders, such as PVDF, may help to prevent voids in the active material layer, low tensile strength exhibited by PVDF may not be sufficient to retain mechanical and electrical connections within an electrode layer during discharge. Among PAA, PVDF, CMC, SBR, and alginates binders, the PAA binder is considered to have the highest tensile strength, followed by CMC, SBR, and alginates, and finally PVDF. However, the tensile strength on its own is not sufficient. The tensile strength needs to be coupled with strong bonding between the binder and active material structure, which is achieved by treating the active materials structures using techniques described herein.

In addition to maintaining electronic conductivity within an electrode, treatment of the active materials structures is believed to help with controlling ionic conductivity. First, electrodes are typically fabricated with a predetermined porosity, such as >30%. The porosity facilitates transport of electrolyte solution to the electrode active materials. The open pores may also help accommodate the volume expansion of the active material structures upon lithiation without causing fracture. The treatment helps with uniform distribution of active material particles throughout the electrode layer and uniform porosity.

Examples of Treatment and Active Materials Structures

Figure 2:
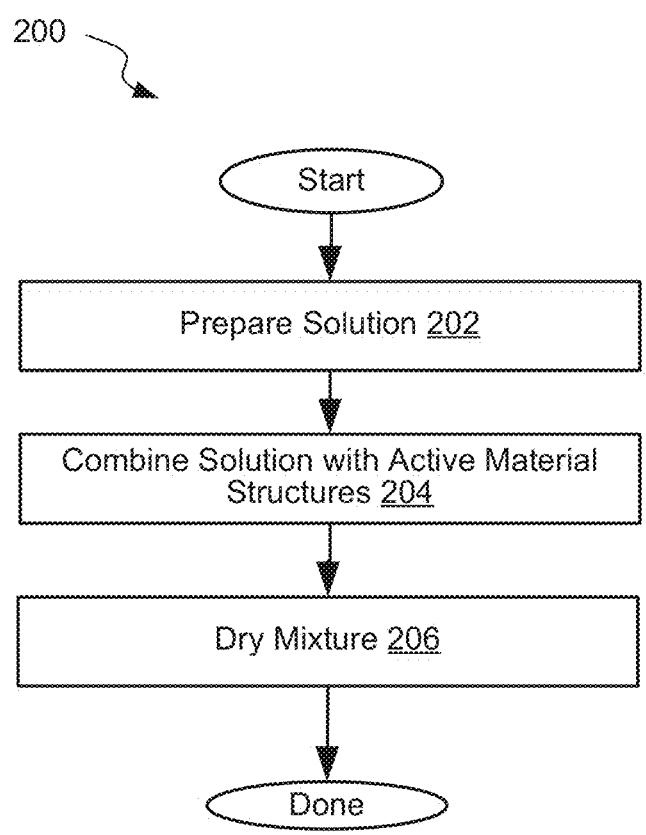
FIG. 2 is a process flowchart of a method for treating active material structures to enhance their bonding characteristics, in accordance with some embodiments.

FIG. 2 is a process flowchart of a method 200 for treating active material structures to enhance their bonding characteristics, in accordance with some embodiments. Method 200 may start with preparing a solution containing a treating agent. Some examples of treating agents include amino-silanes, poly(amines), and/or poly(imines), such as aminopropyltriethoxysilane, aminopropyltrimethoxysilane, bis-gamma-trimethoxysilypropyl amine, aminoneohexyltrimethoxysilane, aminoneohexylmethyldimethoxysilane, poly(ethyleneimine) and polye(allylamine). For example, SILQUEST® Y-15744 (available from Momentive Performance Materials Inc. in Columbus, Ohio) may be dissolved in an acidified mixture of alcohol and deionized water. The volumetric concentration of the treating agent may be between about 0.2% and 10% or, more specifically, between about 1% and 5%. These concentration ranges may be based on the volume of 100 g silicon structures with density 4 g/cc. When using the adsorption technique, treatment of active material, for example, with an aqueous 0.5 wt. % solution of poly(ethyleneimine), will impart the desired surface modification.

Method 200 may proceed with combining the solution (containing the treating agent) with active material structures during operation 204. In some embodiments, the active material structures include silicon, tin, and/or germanium. The structures including silicon may be referred to as silicon containing structures. In some embodiments, the active material structures may include multiple materials, such as silicon and carbon, silicon-tin alloy, or other types of combinations. These multiple materials may be presented in different types of structures or in the same type structures. For example, a solution may be combined with silicon containing structures and carbon containing structures such that the silicon containing structures are not parts of the carbon containing structures at least prior to operation 204. In some embodiments, the same type of structures may include both silicon and carbon prior to operation 204. For example, structures that include silicon cores and carbon shells may be used. In some embodiments, the method may also involve combining the solution with carbon containing structures such that the carbon containing structures form a layer over the silicon containing structures.

In some embodiments, operation 204 may include mixing the solution with the active material particles to ensure uniform distribution of the solution and uniform coverage of the surface of the active material particles with the solution or more specifically with a treating agent. In some embodiments, the temperature of the mixture may be kept at between about 10° C. and 60° C. In the same or other embodiments, the acidity of the mixture may be kept between about 4.5 pH and 5.5 pH, with acetic acid, when using the technique of amino-silanization.

The amount of the treatment agent may depend on the surface area of the active material particles. For example, active material particles with the surface area of 2.65 m²/g may receive between about 0.1 ml and 1 ml of the treatment agent for 100 g of particles or between about 0.1 ml and 1 ml of the treatment agent for 265 m² of the surface area of the active material particles. Excessive amounts of the treatment agent may negatively impact the performance of the cell, generating undesired by-products, or toxicity. The excess amount of the treatment agent may be removed, in some embodiments, by washing off the active material particles using a solvent that does not contain the treating agent. The washing process may be repeated multiple times and controlled by monitoring, for example, a pH level of the washing solution. On the other hand, insufficient amounts of the treatment agent may not provide adequate bonding to the binder. Another factor that may impact the amount of the treatment agent is the material of the active material particles.

Without being restricted to any particular theory, it is believed that amino-silanization of silicon is different from poly(amine) adsorption. In the adsorption process both silicon and the carbon based active material can be surface modified. For example, silicon particles may be treated with an aqueous solution of poly(ethyleneimine) (PEI) to form a mono-molecular adsorbate on the surface of these particles. Once the adsorbate is formed, the particles become positively charged in water. The particles may be combined with carbon containing particles, which are negatively charged in water. This causes an electrostatic association to decorate the silicon particles with carbon based particles and to give composite particles with a negative charge. Any excess of carbon based particles that did not associate with the silicon particles remained negatively charged. Finally, further addition of poly(ethyleneimine) solution may add a positive charge ($=-NRH_2^+$, where R=H or $-CH_2-$) to all particles. To make an electrode, the particle mixture may be dispersed in a binder solution. For example, poly(acrylic acid) partially neutralized with sodium hydroxide may be used. This binder adsorbs to the poly(ethyleneimine) surface layers on the silicon and carbon based particles to form a poly(ammonium acrylate salt). After removal of water and heating that salt converts to a poly(amide) to give a strong interfacial bond between particles and the poly(acrylic acid) matrix.

In some embodiments, before combining active material particles with the solution, the active material particles may be pre-treated to, for example, controllably form an oxide layer on the surface of the particles.

Method 200 may proceed with drying the mixture during operation 206. During this operation, the solvents used to prepare a treatment agent solution may be removed. Drying may be performed in stages. For example, operation 206 may start with air drying, followed by drying at about 60° C. (e.g., for about 2 hours) and finally curing at about 100° C. (e.g., for about 1 hour). Drying in stages ensures smooth removal of the alcohol at a lower temperature and then water at a higher temperature when both alcohol and water are used in the solution. Furthermore, a condensation reaction, in which the Si—O—R linkage is formed, may be triggered at a higher temperature, such as greater than 80° C., such as about 100° C. The condensation reaction establishes bonds between the silane molecule and the silicon particle. This staged drying process also avoids sudden generation of steam within the mixture, which can cause undesirable porosity or other damaging effects. In some embodiments, the drying process involves drying for 24 hrs at a room temperature, followed by 30 minutes at 100° C. or 10 minutes at 120° C.

In some embodiments, operation 206 also involves heat treatment. The heat treatment may adoptively or covalently anchor the one or more treatment materials to the external surfaces of the silicon containing structures. The heat treatment may be performed at a temperature of between about 80° C. and 130° C.

In some embodiments, the treatment agent forms a covalent bond with the surface of the active material particles. As such, the treatment agent becomes an integral part of the active material structures and gets anchored on the surface of these structures. The other end of the treatment agent, which carries the amine group, is available for bonding to the carboxylic acid group on the binder polymer, such as PAA.

Figure 3A:
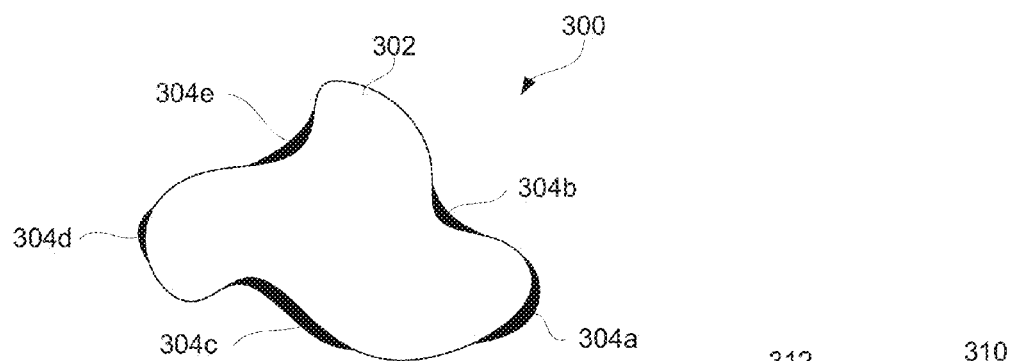
FIG. 3A illustrates a treated active material structure that has portions of its surface covered with a treatment agent, in accordance with some embodiments.
Figure 3B:
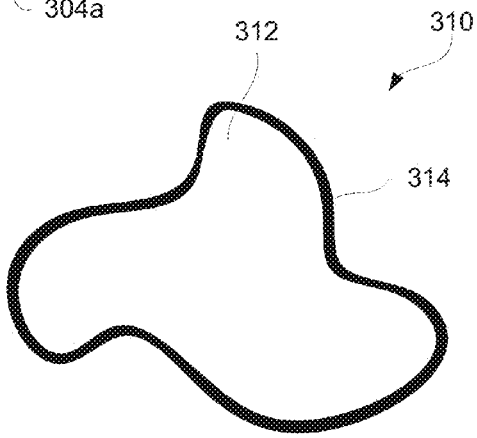
FIG. 3B illustrates a treated active material structure that has its entire surface covered with a treatment agent, in accordance with some embodiments.
Figure 3C:
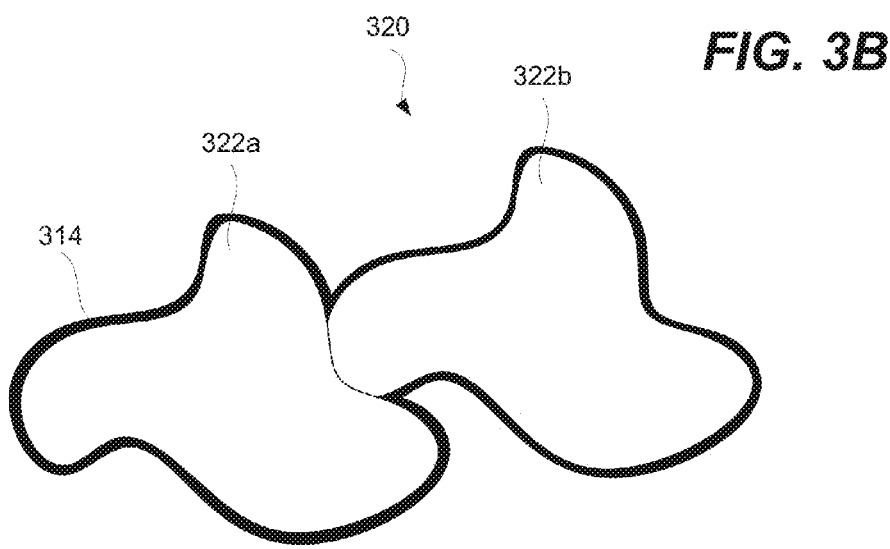
FIG. 3C illustrates a treated active material agglomerate that includes two active material structures enclosed into a shared shell formed by a treatment agent, in accordance with some embodiments.

The output of operation 206 may be active material structures with treated surfaces. The treated active material structures may form soft aggregates that easily disperse during further processing, such as mixing slurry. FIGS. 3A-3C illustrate different examples of treated active material structures. Specifically, FIG. 3A illustrates a treated active material structure 300 that has only portions of its surface covered with a treatment agent forming patches 304a-304e. Portions of original active material structure 302 remain uncovered by the treatment agent. FIG. 3B illustrates a treated active material structure 310 that has its entire surface covered with a treatment agent thereby forming a core 312 of the original active material structure and a shell 314 of the treatment agent. FIG. 3C illustrates a treated active material agglomerate 320 that includes two active material structures 322a and 322b enclosed into the same shell 314. When and if this agglomerate falls apart, portions of active material structures 322a and 322b may remain uncovered.

Examples of Fabrication and Electrochemical Cells

Figure 4:
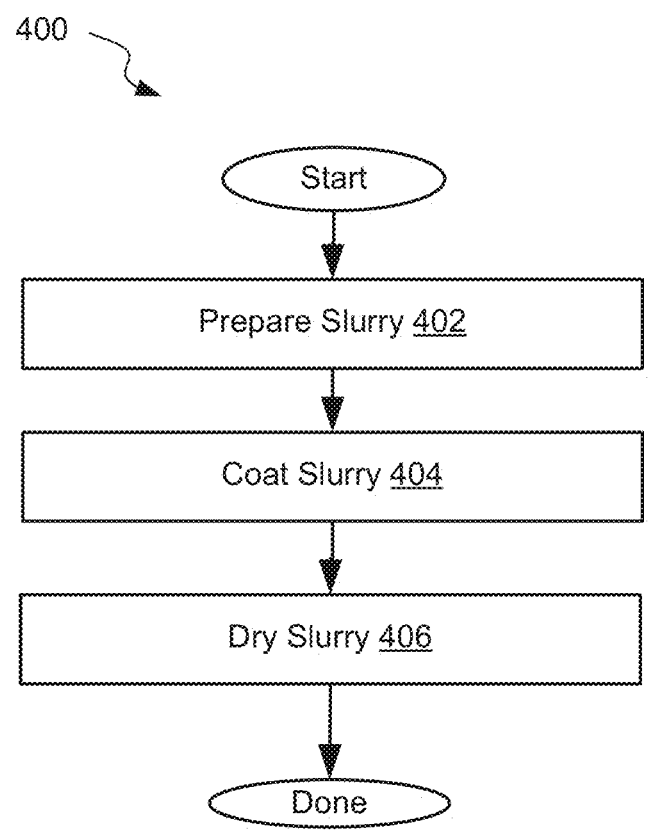
FIG. 4 is a process flowchart corresponding to a method of forming an electrode using treated active material structures, in accordance with some embodiments.

FIG. 4 is a process flowchart corresponding to a method 400 of forming an electrode using treated active material structures, in accordance with some embodiments. Method 400 may start with preparing a slurry during operation 402. The treated active material structures may be mixed with a binder. In some embodiments, multiple different active material structures may be mixed into the same slurry. At least one of these different structures may be treated in accordance with techniques described above. Other types of structures may be untreated. For example, treated silicon particles may be combined in the same slurry with untreated graphite particles.

In some embodiments, silicon particles either surface modified by amino-silanization or by poly(amine) adsorption readily disperse in the aqueous binder solution of partially neutralized (pH ~6) poly(acrylic acid). Carbon-based particles surface modified by poly(amine) adsorption) or after being deposited on the silicon particles and then surface modified by poly(amine) adsorption show the same wetting and dispersion behavior.

Method 400 may proceed with coating the slurry onto a conductive substrate (operation 404) and drying the slurry onto the substrate (operation 406). In some embodiments, in order to reduce effects of delamination and/or deformation of the substrate when the active materials particles expand and contract during cycling, a substrate with a nodular surface may be used. In the same or other embodiments, a substrate may include copper metal alloys or laminates (e.g., copper electroplated on another substrate with a higher mechanical strength), nickel or other metal foil.

Figure 5:
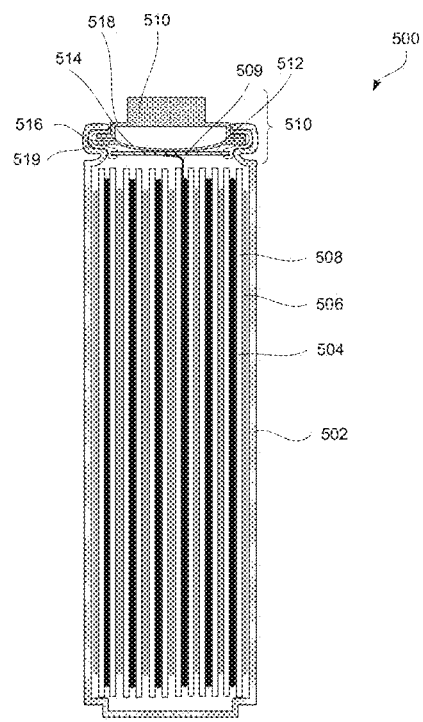
FIG. 5 illustrates a schematic cross-section view of the wound cylindrical cell, in accordance with some embodiments.

FIG. 5 illustrates a schematic cross-section view of the wound cylindrical cell 500, in accordance with some embodiments. Positive electrode 506, negative electrode 504, and separator strips 508 may be wound in to a so-called "jelly roll," which is inserted into a cylindrical case 502. Specifically, the jelly roll includes a spirally wound assembly of positive electrode 506, a negative electrode 504, and two strips of separator 508.

Case 502 may be rigid, in particular for lithium ion cells. Other types of cells may be packed into a flexible, foil-type (polymer laminate) case. A variety of materials can be chosen for case 502. The selection of case materials depend in part on polarity of case 502. If case 502 is connected to positive electrode 506, then case 502 may be formed from titanium 6-4, other titanium alloys, aluminum, aluminum alloys, and 300-series stainless steel. On the other hand, if case 502 is connected to negative electrode 504, then case may be made from titanium, titanium alloys, copper, nickel, lead, and stainless steels. In some embodiments, case 502 is neutral (i.e., have a different potential than the positive electrode or the negative electrode) and may be connected to an auxiliary electrode made, for example, from metallic lithium. An electrical connection between case 502 and an electrode may be established by a direct contact between case 502 and this electrode (e.g., an outer wound of the jelly roll), by a tab connected to the electrode and case 502, and other techniques. Case 502 may have an integrated bottom. Alternatively, a bottom may be attached to the case by welding, soldering, crimping, and other techniques. The bottom and the case may have the same or different polarities (e.g., when the case is neutral).

The top of case 502, which is used for insertion of the jelly roll, may be capped with header assembly 510. In some embodiments, header assembly 510 includes a weld plate 512, a rupture membrane 514, a PTC-based resettable fuse 516, header cup 518, and insulating gasket 519. Weld plate 512, rupture membrane 514, PTC-based resettable fuse 516, and header cup 518 are all made from conductive material and are used for conducting electricity between an electrode (negative electrode 504 in FIG. 5) and cell connector 520 (integrated or attached to header cup 518 in FIG. 5). Insulating gasket 519 is used to support the conductive components of header assembly 510 and insulate these components from case 502. Weld plate 512 may be connected to the electrode by tab 509. One end of tab 509 may be welded to the electrode (e.g., ultrasonic or resistance welded), while the other end of tab may be welded to weld plate 512. Centers of weld plate 512 and rupture membrane 514 are connected due to the convex shape of rupture membrane 514. If the internal pressure of cell 500 increases (e.g., due to electrolyte decomposition and other outgassing processes), rupture membrane 514 may change its shape and disconnect from weld plate thereby breaking the electrical connection between the electrode and cell connector 520.

PTC-based resettable fuse 516 is disposed between edges of rupture membrane 514 and edges of header cup 518 effectively interconnecting these two components. At normal operating temperatures, the resistance of PTC-based resettable fuse 516 is low. However, its resistance increases substantially when PTC-based resettable fuse 516 is heated up due to, e.g., heat released within cell 500. PTC-based resettable fuse is a thermally activated circuit breaker that can electrically disconnect rupture membrane 514 from header cup 518 and, as a result, disconnect the electrode from cell connector 520 when the temperature of PTC-based resettable fuse 516 exceeds a certain threshold temperature. In some embodiments, a cell or a battery pack may use a negative thermal coefficient (NTC) safety device in addition to or instead of a PTC-based resettable fuse.

Header cup 518 is an external component of header assembly 510. It may be attached to or be integrated with cell connector 520. The attachment or integration may be performed prior to forming header assembly 510 and/or attaching header assembly 510 to case 502. As such, high temperatures, mechanical stresses, and other generally destructive characteristics may be used for this attachment and/or integration.

Types of electrochemical cells are determined by active materials used on positive and negative electrodes as well as composition of electrolyte. Some examples of positive active materials include $Li(M'_xM''_y)O_2$, where M' and M" are different metals (e.g., $Li(Ni_xMn_y)O_2$, $Li(Ni_{1/2}Mn_{1/2})O_2$, $Li(Cr_xMn_{1-x})O_2$, $Li(Al_xMn_{1-x})O_2$), $Li(Co_xM_{1-x})O_2$, where M is a metal, (e.g., $Li(Co_xNi_{1-x})O_2$ and $Li(Co_xFe_{1-x})O_2$), $Li_{1-w}(Mn_xNi_yCo_z)O_2$, (e.g., $Li(Co_xMn_yNi_{(1-x-y)})O_2$, $Li(Mn_{1/3}Ni_{1/3}CO_{1/3})O_2$, $Li(Mn_{1/3}Ni_{1/3}Co_{1/3}\text{-}XMg_x)O2$, $Li(Mn_{0.4}Ni_{0.4}Co_{0.2})O_2$, $Li(Mn_{0.1}Ni_{0.1}Co_{0.8})O_2$, $Li_{1-w}(Mn_xNi_xCo_{1-2x})O_2$, $Li_{1-w}(Mn_xNi_yCoAl_w)O_2$, $Li_{1-w}(Ni_xCo_yAl_z)O_2$ (e.g., $Li(Ni_{0.8}Co_{0.15}Al_{0.05})O_2$) $W(Ni_xCo_yM_z)O_2$, Where M is a metal, $Li_{1-w}(Ni_xMn_yM_z)O_2$, Where M is a metal, $Li(Ni_{x-y}Mn_yCr_{2-x})O_4$, $LiM'M''_2O_4$, where M' and M" are different metals (e.g., $LiMn_{2-y-z}Ni_yO_4$, $LiMn_{2-y-z}Ni_yLi_zO_4$, $LiMn_{1.5}Ni_{0.5}O_4$, $LiNiCuO_4$, $LiMn_{1-x}Al_xO_4$, $LiNi_{0.5}Ti_{0.5}O_4$, $Li_{1.05}Al_{0.1}Mn_{1.85}O_{4-z}F_z$, $Li_2MnO_3$) $Li_xV_yO_z$, e.g., $LiV_3O_8$, $LiV_2O_5$, and $LiV_6O_{13}$, $LiMPO_4$ where M is a metal; lithium iron phosphate ($LiFePO_4$) is a common example. It is both inexpensive and has high stability and safety, because the relatively strong phosphate bonds tend to keep the oxygen in the lattice during overcharge, but has poor conductance and requires substantial amounts of conductive additives, $LiM_xM''_{1-x}PO_4$ where M' and M" are different metals (e.g. $LiFePO_4$), $LiFe_xM_{1-x}PO_4$, where M is a metal, $LiVOPO_4 Li_3V_2(PO_4)_3$, $LiMPO_4$, where M is a metal such as iron or vanadium. Further, a positive electrode may include a secondary active material to improve charge and discharge capacity, such as $V_6O_{13}$, $V_2O_5$, $V_3O_8$, $MoO_3$, $TiS_2$, $WO_2$, $MoO_2$, and $RuO_2$.

The selection of positive electrode materials depends on several considerations, such as cell capacity, safety requirements, intended cycle life, etc. Lithium cobalt oxide ($LiCoO_2$) may be used in smaller cells that require higher gravimetric and/or volumetric capacities, such as for portable electronics and medical devices. Cobalt may be partially substituted with Sn, Mg, Fe, Ti, Al, Zr, Cr, V, Ga, Zn, or Cu. Certain materials, such as lithium nickel oxide ($LiNiO_2$), may be less prone to thermal runaway. Other materials provide substantial cost advantage, such as lithium manganese oxide ($LiMnO_2$). Furthermore, lithium manganese oxide has a relatively high power density because its three-dimensional crystalline structure provides more surface area, thereby permitting more ion flux between the electrodes.

Active materials may be deposited as layers on conductive substrates for delivering electrical current between the active materials and cell terminals. Substrate materials may include copper and/or copper dendrite coated metal oxides, stainless steel, titanium, aluminum, nickel (also used as a diffusion barrier), chromium, tungsten, metal nitrides, metal carbides, carbon, carbon fiber, graphite, graphene, carbon mesh, conductive polymers, or combinations of above including multilayer structures. The substrate material may be formed as a foil, films, mesh, laminate, wires, tubes, particles, multi-layer structure, or any other suitable configurations. In one example, a substrate is a stainless steel foil having thickness of between about 1 micrometer and 50 micrometers. In other embodiments, a substrate is a copper foil with thickness of between about 5 micrometers and 30 micrometers. In yet another embodiment, a substrate is an aluminum foil with thickness of between about 5 micrometers and 50 micrometers.

In some embodiments, a separator material may include a fabric woven from fluoro-polymeric fibers of poly(ethylene-co-tetrafluoroethylene (PETFE) and poly(ethylenechloro-co-trifluoroethylene) used either by itself or laminated with a fluoropolymeric microporous film. Moreover, a separator materials may include, polystyrenes, polyvinyl chlorides polypropylene, polyethylene (including LDPE, LLDPE, HDPE, and ultra high molecular weight polyethylene), polyamides, polyimides, polyacrylics, polyacetals, polycarbonates, polyesters, polyetherimides, polyimides, polyketones, polyphenylene ethers, polyphenylene sulfides, polymethylpentene, polysulfones non-woven glass, glass fiber materials, ceramics, a polypropylene membrane commercially available under the designation CELGARD from Celanese Plastic Company, Inc. in Charlotte, N.C., USA, as well as Asahi Chemical Industry Co. in Tokyo, Japan, Tonen Corporation, in Tokyo, Japan, Ube Industries in Tokyo, Japan, and Nitto Denko K.K. in Osaka, Japan. In one embodiment, a separator includes copolymers of any of the foregoing, and mixtures thereof.

A typical separator has the following characteristic: air resistance (Gurley number) of less than about 800 seconds, or less than about 500 seconds in a more specific embodiment; thickness of between about 5 μm and 500 μm, or in specific embodiment between about 10 μm and 100 μm, or more specifically between about 10 μm and 30 μm; pore diameters ranging from between about 0.01 μm and 5 μm or more specifically between about 0.02 μm and 0.5 μm; porosity ranging from between about 20% and 85%, or more specifically, between about 30% and 60%.

The electrolyte in lithium ions cells may be liquid, solid, or gel. Lithium ion cells with the solid electrolyte are also referred to as a lithium polymer cells. A typical liquid electrolyte includes one or more solvents and one or more salts, at least one of which includes lithium. During the first charge cycle (sometimes referred to as a formation cycle), the organic solvent in the electrolyte can partially decompose on the negative electrode surface to form a solid electrolyte interphase layer (SEI layer). The interphase also prevents decomposition of the electrolyte in the later charging subcycles.

Some examples of non-aqueous solvents suitable for some lithium ion cells include the following: cyclic carbonates (e.g., ethylene carbonate (EC), propylene carbonate (PC), butylene carbonate (BC) and vinylethylene carbonate (VEC)), lactones (e.g., gamma-butyrolactone (GBL), gamma-valerolactone (GVL) and alpha-angelica lactone (AGL)), linear carbonates (e.g., dimethyl carbonate (DMC), methyl ethyl carbonate (MEC), diethyl carbonate (DEC), methyl propyl carbonate (MPC), dipropyl carbonate (DPC), methyl butyl carbonate (NBC) and dibutyl carbonate (DBC)), ethers (e.g., tetrahydrofuran (THF), 2-methyltetrahydrofuran, 1,4-dioxane, 1,2-dimethoxyethane (DME), 1,2-diethoxyethane and 1,2-dibutoxyethane), nitriles (e.g., acetonitrile and adiponitrile) linear esters (e.g., methyl propionate, methyl pivalate, butyl pivalate and octyl pivalate), amides (e.g., dimethyl formamide), organic phosphates (e.g., trimethyl phosphate and trioctyl phosphate), and organic compounds containing an S=O or $SO_2$ group (e.g., dimethyl sulfone and divinyl sulfone), and combinations thereof.

Examples of solvents that may be present in the initial electrolyte include cyclic carbonates (e.g., ethylene carbonate (EC) and propylene carbonate (PC)), linear carbonates (e.g., dimethyl carbonate (DMC), diethyl carbonate (DEC) and ethylmethyl carbonate (EMC)), fluorinated versions of the cyclic and linear carbonates (e.g., monofluoroethylene carbonate (FEC)). Furthermore, non-carbonate solvents, such as sulfones, nitriles, dinitriles, esters, and ethers, may be used.

Non-aqueous liquid solvents can be employed in combination. Examples of the combinations include combinations of cyclic carbonate-linear carbonate, cyclic carbonate-lactone, cyclic carbonate-lactone-linear carbonate, cyclic carbonate-linear carbonate-lactone, cyclic carbonate-linear carbonate-ether, and cyclic carbonate-linear carbonate-linear ester. In one embodiment, a cyclic carbonate may be combined with a linear ester. Moreover, a cyclic carbonate may be combined with a lactone and a linear ester. In a specific embodiment, the ratio of a cyclic carbonate to a linear ester is between about 1:9 to 10:0, preferably 2:8 to 7:3, by volume.

A salt for the electrolytes may include one or more of the following: $LiPF_6$, $LiBF_4$, $LiClO_4 LiAsF_6$, $LiN(CF_3SO_2)_2$, $LiN(C_2F_5SO_2)_2$, $LiCF_3SO_3$, $LiC(CF_3SO_2)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, lithium salts having cyclic alkyl groups (e.g., $(CF_2)_2(SO_2)_{2x}Li$ and $(CF_2)_3(SO_2)_{2x}Li$), and combination of thereof. Common combinations include $LiPF_6$ and $LiBF_4$, $LiPF_6$ and $LiN(CF_3SO_2)_2$, $LiBF_4$ and $LiN(CF_3SO_2)_2$.

In one embodiment the total concentration of salt in a liquid non-aqueous solvent (or combination of solvents) is at least about 0.3 M; in a more specific embodiment, the salt concentration is at least about 0.7M. The upper concentration limit may be driven by a solubility limit or may be no greater than about 2.5 M; in a more specific embodiment, no more than about 1.5 M.

Experimental Results

Figure 6A:
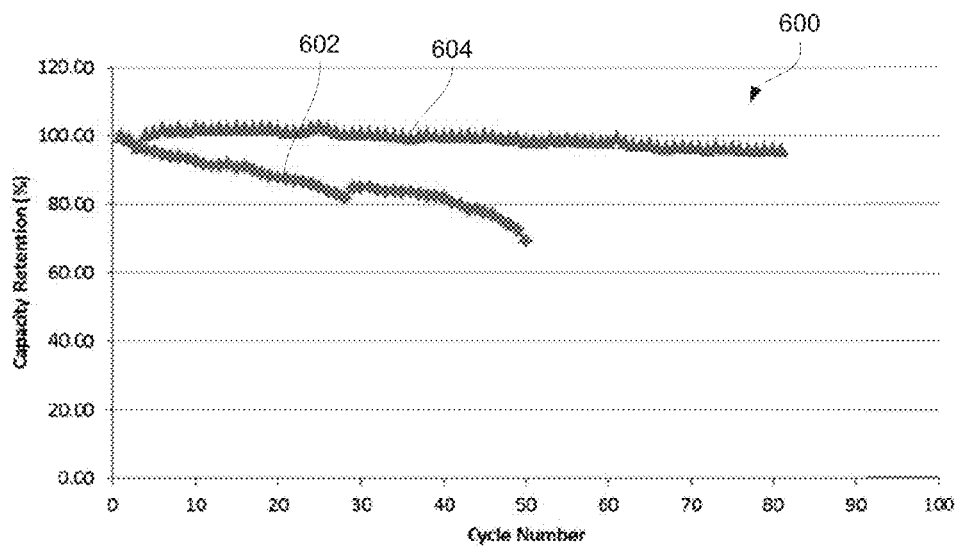
FIG. 6A illustrates a cycling data plot for two cells fabricated using different negative active materials.

FIG. 6A illustrates a cycling data plot 600 for two cells fabricated using different negative active materials. Specifically, line 602 represents cycling data of a control cell fabricated using untreated silicon alloy particles. Line 604 represents cycling data of a controlled cell fabricated using silicon alloy particles treated with aminosilane.

Before treatment the silicon particles were the same as for the control cell. The treatment process involves mixing the silicon particles with a solution of aminofunctional organoalkoxysiloxane, SILQUEST® Y-15644 (available from Momentive Performance Materials Inc. in Columbus, Ohio). For each 100 grams of the silicon particles, 0.25 milliliters of the organoalkoxysiloxane was used. The organoalkoxysiloxane was first dissolved in an acidified mixture of DI water and reagent-grade ethanol to form an organoalkoxysiloxane solution. For each 0.25 milliliters of the organoalkoxysiloxane, 11 milliliters of the alcohol-water mixture, plus a drop of glacial acetic acid, was used. The volume ratio of the alcohol to water in the mixture was 10:1. The drop of glacial acetic acid lowers the pH of the solution to 4.5-5.5. The organoalkoxysiloxane solution was swirled for about five minutes to hydrolyze the alkoxy groups. The freshly prepared organoalkoxysiloxane solution was then added drop-wise to the silicon particles while blending. The silane-treated silicon particles were dried two hours in air at room temperature, followed by two hours in an oven at 60° C. and finally cured for an hour at 100° C. As noted above, staged drying removes the alcohol and water at a moderate rate and prevents steam formation within the mixture. Furthermore, raising the temperature to 100° C., after removing most of the alcohol and water, causes a condensation reaction between the —OH groups in the hydrolyzed organoalkoxysiloxane end of the molecule and the Si—OH groups on the surface of the silicon particles. This condensation reaction forms a Si—O—R type of link between the silicon particles and the siloxane additives. The organoalkoxysiloxane treated silicon particles were then used in preparation of a slurry, electrode, and cell in accordance to the procedure described above with reference to the control cell.

Both cells had negative electrodes including 60% by weight of the silicon particles (treated or untreated), 28% by weight of graphite, 2% by weight of conductive carbon (Super P), and 10% by weight of PAA binder. Half-cells were constructed using these negative electrodes. Lithium metal was used as a positive electrode. The electrolyte included a mixture of ethylene carbonate, di-ethylene carbonate, $LiPF_6$, and imide salts, as well as an additive.

Both cells were cycled at the same conditions. Cycling was performed between 0.005V and 0.9 V. The first two cycles were performed at a rate of C/20, respectively, followed by continuous cycling at C/5. As could be seen from FIG. 6A, the cell fabricated using the organoalkoxysiloxane treated silicon particles demonstrated much longer and more stable cycle life in comparison with the cell fabricated using the untreated silicon particles (i.e., the control cell). The capacity of the control cell started fading below 80% of the initial capacity after only 40 cycles, while the capacity of the cell with the organoalkoxysiloxane treated silicon particles maintained more than 95% of its initial capacity even after 80 cycles. Without being restricted to any particular theory, it is believed that some of the untreated silicon structures become electrically disconnected from the current collector due to their separation from other conductive materials in the electrode. This separation is believed to be caused by the weak bond between the untreated silicon structures and the binder. On the other hand, the treated silicon structures form stronger bonds to the binder and this bond held these treated silicon structures to better maintain the electrical connections to other conductive materials in the electrode and as a result to the current collector.

Figure 6B:
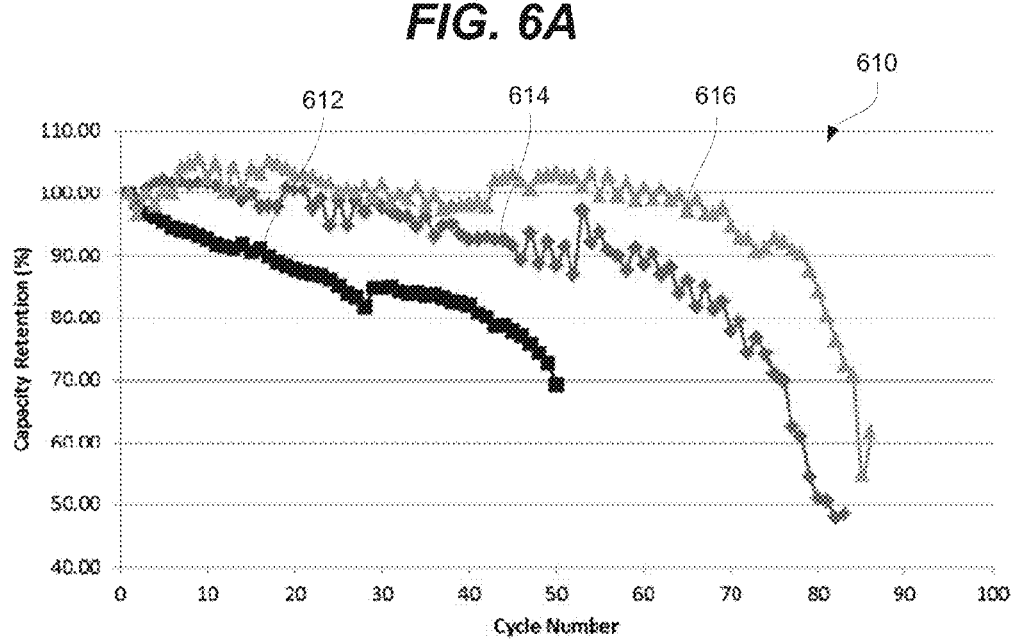
FIG. 6B illustrates a cycling data plot for three cells fabricated using different negative active materials.

FIG. 6B illustrates a cycling data plot 610 for three cells fabricated using different negative active materials. Specifically, line 612 represents cycling data of a controlled cell fabricated using untreated silicon particles as described above with reference to FIG. 6A. Line 614 represents cycling data of a cell fabricated using silicon particles treated with silane. The silane treatment is explained below. Line 616 represents cycling data of a cell fabricated using silicon particles treated with poly(ethyleneimine) (PEI).

As could be seen from FIG. 6B, the cell fabricated using the PEI treated silicon particles demonstrated much longer and more stable cycle life than the cell fabricated using the untreated silicon particles (i.e., the control cell). The capacity of the cell with the PEI treated silicon particles maintained more than 90% of its initial capacity even after 80 cycles. Without being restricted to any particular theory, it is believed that PEI treatment improves adhesion between the particles and the binder resulting in more robust electrical connections to other conductive materials in the electrode and as a result to the current collector.

Line 614 displays the performance of amino-silanized silicon while line 616 that of polyamine (PEI) treated silicon. Line 612 represents the performance of a control, using untreated silicon. For the poly(amine) adsorption, 40 g of silicon particles were mixed with 80 mL of a poly(ethyleneimine) (PEI) solution. The solution included 0.2% of PEI (Sigma Aldrich, Part #181978; MW ~750,000) in water (pH 9-10, paper). The mixture was placed into a polyethylene bottle and shaken using Burrell Wrist Action Shaker for about 9 hours. About 5 g of that dispersion was removed for other experiments. The remainder was centrifuged at 11,000 rpm for 15 min using Eppendorf #5804 tubes to give a cake and a clear supernatant of pH ~9. The cake was freed of adherent PEI solvent by re-dispersion in water followed by centrifugation. The process was repeated two times when the pH of the supernatant was the same as that of water (~7). The cake was transferred to a poly(ethylene) bottle and re-dispersed in ~80 mL of water. To that dispersion was added 17.92 g of graphite (CGP G5) and 1.28 g of carbon black (Super P). The mixture was agitated using Burrell Wrist Action Shaker for about 2 hours and then centrifuged at 11,000 rpm for 15 min. The supernatant was decanted and the cake was dispersed in ~80 mL of 0.01% PEI solvent and shaken using Burrell Wrist Action Shaker for 1 hour followed by centrifugation at 11,000 rpm for 15 min and decantation of the supernatant. The supernatant had a slight "sheen" on top believed to be graphite. Its amount was estimated to be <50 mg. The cake was re-dispersed one more time in 0.01% PEI solution and centrifuged. A part of the wet cake in the centrifuge tubes was transferred to a Petri dish, while some was left in the tubes. The product in both the Petri dish and the tubes was dried at room temperature at low pressure created by an oil vacuum pump vacuum for 2 hour and then at 70° C. vacuum overnight. The dry product was a fluffy gray powder, which was transferred to a polyethylene jar. The powder in the polyethylene jar was shaken using Burrell Wrist Action Shaker for 3 hours to break up aggregates. 53 g of product was recovered.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. An active material for use in electrochemical cells, the active material comprising a powder formed by discrete particles, each particle in the powder comprising:
   a silicon containing structure comprising a core and an external surface;
   a treatment layer covering at least a portion of the external surface of the silicon containing structure,
      wherein the treatment layer comprises one or more treatment materials selected from the group consisting of an aminosilane, a poly(amine), a poly(imine), and an amine functionalized alkoxy siloxane; and
   a carbon shell covering at least a portion of the treatment layer,
      wherein the carbon shell comprises carbon particles having a particle size of less than 1 micrometer.

2. The active material of claim 1, wherein the one or more treatment materials comprise one or more aminosilanes selected from the group consisting of aminopropyltriethoxysilane, aminopropylmethoxysilane, bis-gamma-trimethoxysilylpropyl amine, aminoneohexyltrimethoxysilane, and aminoneohexylmethyldimethoxysilane.

3. The active material of claim 1, wherein the one or more treatment materials comprise one or more materials selected from the group consisting of poly(ethyleneimine), poly(allylamine), and poly(vinylamine).

4. The active material of claim 1, wherein a volume ratio of the treatment layer to the silicon containing structure is between about 0.001% and 10%.

5. The active material of claim 1, wherein a volume ratio of the treatment layer to the silicon containing structure is less than about 0.1%.

6. The active material of claim 1, wherein the treatment layer is formed by molecules of the one or more treatment materials adsorbed on the external surface of the silicon containing structure.

7. The active material of claim 1, wherein the treatment layer is formed by molecules of the one or more treatment materials covalently bound to the external surface of the silicon containing structure.

8. The active material of claim 7, wherein the one or more treatment materials comprise amine functionalized alkoxy siloxane.

9. The active material of claim 8, wherein the one or more treatment materials form oligomeric brushes extending away from the external surface of the silicon containing structure.

10. The active material of claim 1, wherein the external surface of the silicon containing structure comprises silicon dioxide.

11. The active material of claim 1, wherein the treatment layer comprises a poly(imine).

12. The active material of claim 1, wherein the silicon containing particle has a size of between about 1 and 50 microns.

13. A method of fabricating an active material comprising a powder of discrete surface treated silicon containing particles for use in electrochemical cells, the method comprising:
preparing a solution,
the solution comprising a carrier solvent and one or more treatment materials,
wherein the carrier solvent comprises a mixture of alcohol and deionized water, and
wherein the one or more treatment materials are selected from the group consisting of an aminosilane, a poly(amine), a poly(imine), and an amine functionalized alkoxy siloxane;
combining the solution with discrete silicon containing structures,
wherein each of the discrete silicon containing structures comprises a core and an external surface,
wherein the one or more treatment materials of the solution attach to the external surface of each of the discrete silicon containing structures when the solution is combined with the discrete silicon containing structures; and
removing the carrier solvent from a combination of the discrete silicon containing structures and the solution while retaining the one or more treatment materials on the external surface of each of the discrete silicon containing structures;
after removing the carrier solvent from the combination of the discrete silicon containing structures and the solution, performing a heat treatment on the discrete silicon containing structures having the one or more treatment materials attached to the external surface,
wherein the heat treatment adoptively or covalently anchors the one or more treatment materials to the external surface of each of the discrete silicon containing structures; and
combining carbon containing structures having a particle size of less than 1 micron with the discrete silicon containing structures having the one or more treatment materials on the external surface,
wherein combining the carbon containing structures with the discrete silicon containing structures forms a carbon shell at least partially covering the one or more treatment materials on the external surface of the discrete silicon containing structures.

14. The method of claim 13, wherein an acidity of the solution is maintained at between about 4.0 pH and 6.0 pH for amino-silanization.

15. The method of claim 13, wherein the heat treatment is performed at a temperature of between about 80° C. and 130° C.

16. The method of claim 13, further comprising combining the solution with carbon containing structures, wherein the carbon containing structures form a layer over the silicon containing structures.

17. The method of claim 13, wherein a volume ratio of the alcohol to water is 10:1.

18. The method of claim 17, wherein the alcohol is ethanol.

19. A method of fabricating an electrode for a lithium ion cell, the method comprising:
preparing a solution,
the solution comprising a carrier solvent and one or more treatment materials,
wherein the carrier solvent comprises a mixture of alcohol and deionized water, and
wherein the one or more treatment materials are selected from the group consisting of an aminosilane, a poly(amine), a poly(imine), and an amine functionalized alkoxy siloxane;
combining the solution with discrete silicon containing structures,
wherein each of the discrete silicon containing structures comprises a core and an external surface,
wherein the one or more treatment materials of the solution attach to the external surface of each of the discrete silicon containing structures; and
removing the carrier solvent from a combination of the discrete silicon containing structures and the solution while retaining the one or more treatment materials on the external surface of each of the discrete silicon containing structures; and
after removing the carrier solvent from the combination of the discrete silicon containing structures and the solution, performing a heat treatment on the discrete silicon containing structures having the one or more treatment materials attached to the external surface,
wherein the heat treatment adoptively or covalently anchors the one or more treatment materials to the external surface of each of the discrete silicon containing structures;
combining carbon containing structures having a particle size of less than 1 micron with the discrete silicon containing structures having the one or more treatment materials on the external surface,
wherein combining the carbon containing structures with the discrete silicon containing structures forms a carbon shell at least partially covering the one or more treatment materials on the external surface of the discrete silicon containing structures;
forming a slurry comprising of the discrete silicon containing structures, water, and a binder,
wherein the binder is selected from the group consisting of poly acrylic acid (PAA), styrene butadiene (SBR), and an alginates;
coating the slurry onto a current collector substrate; and
drying the slurry to form the electrode.

* * * * *